United States Patent
Krammer-Lukas et al.

(10) Patent No.: US 10,357,501 B2
(45) Date of Patent: Jul. 23, 2019

(54) TREATING CONDITIONS ASSOCIATED WITH INCREASED EOTAXIN WITH 25-HYDROXYVITAMIN D3

(71) Applicant: DSM IP ASSETS B.V., Heerlen (NL)

(72) Inventors: Stephanie Krammer-Lukas, Basel (CH); Elisabeth Stoecklin, Basel (CH); Joseph Schwager, Basel (CH); Swen Wolfram, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 12 days.

(21) Appl. No.: 15/393,160

(22) Filed: Dec. 28, 2016

(65) Prior Publication Data

US 2017/0106005 A1 Apr. 20, 2017

Related U.S. Application Data

(63) Continuation of application No. 13/990,569, filed as application No. PCT/EP2011/071684 on Dec. 5, 2011, now abandoned.

(30) Foreign Application Priority Data

Dec. 6, 2010 (EP) .................................... 10193847

(51) Int. Cl.
| | | |
|---|---|---|
| *A61K 31/59* | (2006.01) | |
| *A61K 47/00* | (2006.01) | |
| *A61K 31/593* | (2006.01) | |
| *A23L 33/155* | (2016.01) | |
| *A61K 9/00* | (2006.01) | |
| *A61K 9/48* | (2006.01) | |

(52) U.S. Cl.
CPC .......... *A61K 31/593* (2013.01); *A23L 33/155* (2016.08); *A61K 9/0053* (2013.01); *A61K 9/48* (2013.01); *A23V 2002/00* (2013.01)

(58) Field of Classification Search
CPC .............................. A61K 31/59; A61K 31/593
USPC ....................................................... 514/168
See application file for complete search history.

(56) References Cited

U.S. PATENT DOCUMENTS

| | | |
|---|---|---|
| 2008/0038410 A1 | 2/2008 | Giordano |
| 2011/0052707 A1 | 3/2011 | Buck et al. |

FOREIGN PATENT DOCUMENTS

| | | |
|---|---|---|
| CN | 101668532 | 3/2010 |
| JP | 58-216178 | 12/1983 |
| JP | 10-87495 | 4/1998 |
| JP | 2000191537 | 7/2000 |
| JP | 2010-525050 | 7/2010 |
| WO | 90/06754 | 6/1990 |
| WO | 98/18468 | 5/1998 |
| WO | 2008/134523 | 11/2008 |
| WO | 2009/047644 | 4/2009 |
| WO | 2009/101132 | 8/2009 |
| WO | WO-2009101132 A1 * | 8/2009 ........... A61K 31/592 |

OTHER PUBLICATIONS

Bozzetto, et al., European Journal of Allergy and Clinical Immunology, Aug. 15, 2011, Allergy 2011; DOI: 10.1111/j.1398-9995.2011.02711.*
Huh et al. "Vitamin D deficiency in children and adolesents: Epidemiology, impact and treatment," Rev. Endor. Metab. Dirord. 2008, vol. 9, pp. 161-170 (Year: 2008).*
Clifford et al. "Vitamin D—a new treatment for airway remodeling in asthma?" British J. Pharmacology, 2009, vol. 158, 1426-1428 (Year: 2009).*
Laino "Low vitamin D levels linked to Asthma," WebMD Archives, Mar. 3, 2010, https://www.webmd.com/asthma/news/20100303/low-vitamin-d-levels-linked-to-asthma (Year: 2010).*
International Search Report for PCT/EP2011/071684, dated Feb. 3, 2012.
Written Opinion for PCT/EP2011/071684, dated Feb. 3, 2012.
International Preliminary Report on Patentability dated Jun. 12, 2013.
Aloia, J.F. et al, :Vitamin D. intake to attain a desired serum 25-hydroxyvitamin D concentration, The American Journal of Clinical Nutrition, 2008, 87:1952-8.
Enzo Emanuele, et al., "Association of plasma eotaxin levels with the presence and extend of angiographic coronary artery disease," Atherosclerosis 186 (2006) 140-145.
Agnieszka Burzyfiska, et al, Synthesis of 25-Hydroxyvitamin D3—Calcifediol From Vitamin D2, See On-line Journal of V Multidyscyplinarna Konferencja Nauki o Leku, Submitted: Jan. 25, 2006 09:24, Revised: Jun. 7, 2009 00:44.
Bikle, D.D. Journal of Bone and Mineral Research, vol. 22, Supplement 2, 2007, p. V50, doi: 10.1359/JBMR.07S208 © 2007 American Society for Bone and Mineral Research.
CN Appln. No. 201180058557.5, Official Action dated May 15, 2015.
Fiset et al., "Eotaxin is involved with Asthma, atopic dermatitis, allergic rhinitis and sinusitis", *J Allergy Clin Immunol* 118. 2006:536-8.
Fulkerson et al., "Eotaxin -1, -2, -3 are involved in regulating eosinophil accumulation into the GA tract and other tissues", *Best Pract Clin Gastroenterol*. 2008. 22(3):411-423.
Hogan et al., "Links between lung inflammatory conditions and gastrointestinal inflammatory conditions" *Ailment Pharmacol Ther*. 2004. 20:1231-1240.
Rankin et al., "General Information regarding the range of diseases where eotaxin plays a role", *Mol Medicine Today*. 2000. 6:20-26.
Takeno et al, "Pathological Mechanisms and Clinical Features of Eosinophilic Chronic Rhinosinusitis in the Japanese Population," Allergology International, 2010;59:247-256.

(Continued)

*Primary Examiner* — Shengjun Wang
(74) *Attorney, Agent, or Firm* — Nixon & Vanderhye P.C.

(57) ABSTRACT

Methods for treating/preventing conditions associated with an increased level of eotaxin in a human with 25-hydroxyvitamin D3 (calcifediol) are provided. Optionally, vitamin D3 may be used together with 25-hydroxyvitamin D3.

8 Claims, No Drawings

(56) References Cited

OTHER PUBLICATIONS

JP Office Action of Patent Application No. P2013-541379 dated Nov. 4, 2015.
Matheu, et al, "Dual effects of vitamin D-induced alteration of $T_H1/T_H2$ cytokine expression: Enhancing IgE production and decreasing airway eosinophilia in murine allergic airway disease," Journal of Allergy and Clinical Immunology, vol. 112, No. 3, pp. 585-592, Sep. 2003.
The Journal of Practical Medicine, vol. 26, Issue 19, doi 10.3969/j.issn. 1006-5725.2010.19.010, pp. 3488-3490.

* cited by examiner understand# TREATING CONDITIONS ASSOCIATED WITH INCREASED EOTAXIN WITH 25-HYDROXYVITAMIN D3

CROSS-REFERENCE

This application is a continuation of commonly owned U.S. application Ser. No. 13/990,569, filed May 30, 2013 (now abandoned), which is the national phase application under 35 USC § 371 of PCT/EP2011/071684, filed Dec. 5, 2011, which designated the US and claims priority to European Patent Application No. 10193847.0, filed Dec. 6, 2010, the entire contents of each of which are hereby incorporated by reference.

FIELD OF THE INVENTION

The present invention relates to treating/preventing conditions associated with an increased level of eotaxin in a human with 25-hydroxyvitamin D3 (calcifediol). Optionally, vitamin D3 may be used together with 25-hydroxyvitamin D3.

BACKGROUND OF THE INVENTION

Vitamin D (e.g., ergocalciferol and cholecalciferol) is a group of fat-soluble compounds defined by their biological activity. A deficiency of vitamin D causes rickets in children and osteomalacia in adults. But toxicity can occur after chronic intake of more than 100 times the recommended daily allowance (i.e., 5-15 µg or 200-600 IU vitamin D) for several months. For vitamin D, "The threshold for toxicity is 500 to 600 mcg/kg body weight per day. In general, adults should not consume more than three times the RDA for extended period of time" (Garrison & Somer, *The Nutrition Desk Reference, Third Ed.*, McGraw-Hill, pg. 82, 1997). Hypercalcemia may occur at a blood concentration of 25-hydroxyvitamin D greater than 375 nmol/L. More recently, a safe upper level of Vitamin D was identified to be at least 250 µg/day (10'000 IU) (Hathcock et al. *Am. J Clin. Nutr.* 85:6-18, 2007). Ingestion of such as a dietary supplement has been shown to result in a blood concentration of about 200 nmol/L 25-hydroxyvitamin D.

Vitamin D is a prohormone which has to be hydroxylated in the liver to produce 25-hydroxyvitamin D (calcifediol; 25-OH vitamin D; 25-OH D), which then undergoes another hydroxylation in the kidney and other tissues to produce 1,25-dihydroxyvitamin D, the active hormone form of vitamin D. 1,25-dihydroxyvitamin D is released into the blood, binds to vitamin D binding protein (DBP), and is transported to target tissues. Binding between 1,25-dihydroxyvitamin D and vitamin D receptor allows the complex to act as a transcription factor in the cell's nucleus.

Vitamin D deficiency may promote resorption of bone. It may also modulate function of the cardiovascular, immune, and muscular systems. Epidemiological studies find associations between vitamin D intake and its effect on blood pressure or glucose metabolism. The activity of vitamin D is under negative feedback control by parathyroid hormone.

Both Vitamin D and 25-OH D3 have been administered as pharmaceuticals in the past. Vitamin D, is of course widely available; 25-OH D3 was previously sold in the USA by Organon USA under the name "CALDEROL", but is currently on the FDA's list of discontinued drugs. It was a gelatine capsule containing corn oil and 25-OH D3.

A liquid form of 25-OH D3 has been sold in Spain by FAES Farma under the name "HIDROFEROL" in an oil solution.

The combination of vitamin D and 25-OH D3 has been used in animal feed. 25-OH D3 for use in feed is commercially available from DSM under the name "ROVIMIX HY-D". Tritsch et al. (U.S. Pat. No. 7,632,518) disclose a feed premix composition of at least 25-OH D3 in an amount between 5% and 50% (wt/wt) dissolved in oil and an antioxidant, an agent encapsulating droplets of 25-OH D3 and oil, and a nutritional additive (e.g., Vitamin D3). The premix may be added to poultry, swine, canine, or feline food. This composition stabilizes 25-OH D3 against oxidation.

Simoes-Nunes et al. (US 2005/0064018) discloses adding a combination of 25-OH Vitamin D3 and Vitamin D3 to animal feed. In particular, about 10 µg/kg to about 100 µg/kg of 25-OH Vitamin D3 and about 200 IU/kg to about 4,000 IU/kg of Vitamin D3 are added to swine feed. This addition improves the pig's bone strength.

Stark et al. (U.S. Pat. No. 5,695,794) disclose adding a combination of 25-OH Vitamin D3 and Vitamin D3 to poultry feed to ameliorate the effects of tibial dyschondroplasia.

Borenstein et al U.S. Pat. No. 5,043,170 discloses the combination of Vitamin D3 and either 1-alpha-hydroxycholecalciferol or 1 alpha, 25-dihydroxycholecalciferol to improve egg strength and leg strength in laying hens and older hens.

Chung et al, WO 2007/059960 discloses that sows fed a diet containing both Vitamin D3 and 25-hydroxVitamin D3 had improved general health status, body frame, litter size and health, and other production parameters. Also a 25-OH D3 human food supplement is disclosed, but its dosage range, 5-15 micrograms per kg body weight, which equals to an extremely high daily dosage of 300-900 micrograms per human is very high.

To our knowledge the prior art does not teach or suggest use of 25-hydroxy vitamin D3 as a medicament for humans to treat or prevent conditions associated with an increased eotaxin level.

BRIEF DESCRIPTION OF THE INVENTION

It has been found that 25-hydroxyvitamin D3 (calcifediol) can be used as a nutriceutical, food, food supplement or a medicament to reduce levels of eotaxin, a cytokine involved in eosinophil recruitment. The nutraceutical, food, food supplement or medicament may optionally further comprise vitamin D3 (cholecalciferol). The human may be any age, including children and juveniles, starting from birth to adulthood, from 18 years to 80 years of age, or more than 80 years of age. Forms and dosages of a nutraceutical, food, food supplement and pharmaceutical composition, as well as processes for manufacturing these forms are also disclosed.

One embodiment of this invention is a method of reducing eotaxin levels comprising administering 25-hydroxyvitamin D3 to a human, and observing or appreciating a reduction of symptoms associated with high eotaxin levels is provided. In a healthy person, eotaxin levels in blood serum are low at about 30 pg/ml. If the person suffers from a condition where eotaxin levels are elevated, then the level of eotaxin generally increases, i.e. it can be greater than 50 picograms/ml. There are considerable individual variations of the eotaxin level, but generally speaking, any increased level of eotaxin relates to an increased activity of eosinophils and therefore are related to conditions such as asthma, allergy, or others detailed below.

Administration of 25-OH D3 allows eotaxin levels be reduced to or maintained at a lower level than was present previously, and preferably to a level significantly lower than that observed before administration. Thus, invention also relates to the use of 25-OH D3 for the method of making a medicament useful for reducing levels of eotaxin, maintaining a reduced level of eotaxin, and/or reducing symptoms of conditions related to high eotaxin. This invention also relates to a method of reducing eotaxin levels in an individual in need thereof comprising the steps of: establishing a baseline eotaxin level, administering 25-OH D3, and observing a reduction of eotaxin levels relative to baseline.

The administration may be in the form of a nutraceutical, a food, a food supplement or a medicament. Optionally, vitamin D3 may be administered together with or separately from 25-hydroxyvitamin D3.

Another embodiment of this invention is a method of treating a symptom related to an increase in eotaxin levels comprising administering an eotaxin-reducing amount of 25-OH D3 to a person in need of such a treatment, and observing or appreciating the lessening of the symptom/eotaxin level. This may be done by assaying the amount of eotaxin, or by observing the level of the symptom. Optionally vitamin D3 may be co-administered.

Further aspects will be apparent from the following description and claims, and generalizations thereto.

DETAILED DESCRIPTION OF THE INVENTION

As used throughout the specification and claims, the following definitions apply:

"Vitamin D" means either Vitamin D3 (cholecalciferol) and/or Vitamin D2 (ergocaciferol). Humans are unable to make Vitamin D2 (ergocalciferol), but are able to use it as a source of Vitamin D. Vitamin D2 can be synthesized by various plants and is often used in Vitamin D in supplements as an equivalent to Vitamin D.

"Vitamin D metabolite" means any metabolite of Vitamin D other than 25-hydroxy vitamin D3.

"25-OH D3" refers specifically to 25-hydroxyvitamin D3.

"25-OH D" refers to the 25-hydroxylated metabolite of either Vitamin D2 or Vitamin D3 which is the major circulating form found in plasma.

"Prevent" is meant to include amelioration of the disease, lessening of the severity of the symptoms, early intervention, and lengthening the duration of onset of the disease, and is not intended to be limited to a situation where the patient is no longer able to contract the disease nor experience any symptoms.

Eotaxins (also called CCL-11, CCL-24, and CCL-26) are three proteins which belong to the CC family of chemokines. They are selective recruiters of eosinophils, and also induce the aggregation of eosinophils. Eosinophils play an important beneficial role in killing some invasive microbes and helminths, especially in the gut. Recent studies also suggest a role in organogenesis, tissue repair, and immune regulation.

However, abnormally high amounts of eosinophils in the circulation and in some tissues are characteristic of many pathologies, including allergic diseases (including asthma, rhinitis, and atopic dematitis), other inflammatory disorders (including inflammatory bowel disease, eosinophilic gastroenteritis, and pneumonia), non-allergenic inflammation (such as that induced by ozone inhalation or foreign body granlomatous reactions) as well as some malignancies (such as Hodgkin's disease and various leukemias).

It has been surprisingly found that administration of 25-OH D3 lowered the level of eotaxin in the serum of postmenopausal women. The group receiving 25-OH D3 had a statistically significant lower amount compared to the group receiving vitamin D3. Both 25-hydroxy vitamin D3 and vitamin D3 lowered eotaxin amounts compared to placebo.

Thus, administration of 25-OH D3 would be beneficial for treatment and prevention of diseases and symptoms associated with high levels of eotaxin, as detailed below.

Diseases/Conditions Associated with High Levels of Eotaxins

Asthma

As explained in Pease et al, 2001 *Curr. Opinion in Pharmacol.* 1 (3): 248-253, which is hereby incorporated by reference, one of the characteristic features of asthma is the accumulation of eosinophils in the bronchial walls. When the eosinophils release their contents (including major basic protein), tissue damage and bronchial hyperreactivity, the hallmark of asthma, occur. Individuals diagnosed with asthma have been found to have an increased eotaxin level, and those experiencing acute asthma have been reported to have higher levels than those with stable asthma. Similarly, individuals having occupational asthma were also seen to have higher eotaxin levels.

In mice models, a disruption of the eotaxin gene resulted in a reduction of eosinophil recrutment in an asthma mode. Similarly, administration of an eotaxin-neutralizing antibody also was found to reduce lung esophilila.

Thus another aspect of this invention is a method to decrease the symptoms of asthma by administering a eotaxin-reducing effective amount of 25-OH D3 to a person in need of such reduction. The resulting reduction of eosinophil aggregation would lead to an observable reduction in symptoms of asthma, notably the easing of bronchial restriction. Another aspect of this invention is the use of 25-OH D3 in the method of making an asthma medicament.

The 25-OH D3 may be used as an adjunct to or in co-therapy with known asthma medicaments and/or therapies.

Allergic rhinitis and sinusitis Eotaxin was found to be present in epithelial and inflammatory cells in nasal passages of individuals with allergic rhinitis and sinusitis. (See Fiest et al 2006 *J Allergy Clin Immunol* 118:536-8, which is hereby incorporated by reference). Thus eotaxin is a target for reduction in these conditions. Atopic asthma refers to allergic conditions such as hayfever and allergic dermatits. Increased expression of eotaxin has been observed in these conditions, as well.

Thus another aspect of this invention is a method to decrease the symptoms of allergic rhinitis or sinusitis by administering a eotaxin-reducing effective amount of 25-OH D3 to a person in need of such reduction. The resulting reduction of eosinophil aggregation would lead to an observable reduction in symptoms of rhinitis or sinusitis, including decrease in swelling and inflammation. Another aspect of this invention is the use of 25-OH D3 in the method of making a medicament suitable for rhinitis or sinusitis.

The 25-OH D3 may be used as an adjunct to or in co-therapy with known rhinitis or sinusitis medicaments and/or therapies.

Thus another aspect of this invention is a method to decrease the symptoms of or hayfever or allergic dermatitis by administering a eotaxin-reducing effective amount of 25-OH D3 to a person in need of such reduction. The resulting reduction of eosinophil aggregantion would lead to an observable reduction in symptoms of hayfever or allergic dermatis, including decrease in swelling and inflammation. Another aspect of this invention is the use of 25-OH D3 in the method of making a medicament suitable for hayfever or allergic dermatitis.

The 25-OH D3 may be used as an adjunct to or in co-therapy with known hayfever or allergic dermatitis medicaments and/or therapies.

Nasal Polyps

Chronic inflammatory diseases of the nose and sinuses can lead to the formation of nasal polyps, and this involves an up-regulation of eotaxin (see Rankin et al 2000 *Molecular Medicine Today* 6:20-27, which is hereby incorporated by reference. Administration of 25-OH D3, and/or Vitamin D3, in accordance with this invention will decrease eotaxin levels, and thus ameliorate, prevent or treat the formation and growth of nasal polyps. The 25-OH D3 may be used as an adjunct to or in co-therapy with known medicaments and/or therapies for nasal polyps.

Gastric Disorders

Normally, eosinophils are not found in the esophageal mucosa, but it some disease states, they can accumulate there, having a proinflammatory effect. There are several gastric disorders which involve the presence of eosinophils and increased eotaxin in the gut:

Eosinophilic Esophagitis

Normally, eosinophils are not found in the esophageal mucosa, but it esinophilic esophagitis, they can accumulate there, having a pro-inflammatory effect. Symptoms include dysphagia, chest pain and food impaction. In children, it can include nausea and vomiting, weight loss, anemia and failure to thrive. Often patients have a history of allergies, including food allergies to high protein foods such as milk, eggs, soybean, wheat, chicken and nuts. The eosinophils in the esophageal mucosa release major basic protein, which induces smooth muscle contractions, that are thought to be mechanistically similar to the broncho-constriction observed in asthma. Thus, reducing the amount of eotaxins would ameliorate the symptoms of eosinophilic esophagitis.

Thus another aspect of this invention is a method to decrease the symptoms of eosinophilic esophagitis by administering a eotaxin-reducing effective amount of 25-OH D3 to a person in need of such reduction. The resulting reduction of eosinophil aggregantion would lead to an observable reduction in symptoms of eosinophilic esophagitis, including decrease in smooth muscle contraction, dysphagia, chest pain, food impaction, nausea, and vomiting. Another aspect of this invention is the use of 25-OH D3 in the method of making a medicament suitable for eosinophilic esophagitis.

The 25-OH D3 may be used as an adjunct to or in co-therapy with known eosinophilic esophagitis medicaments.

Inflammatory Bowel Disease (IBS), Crohn's Disease, and Ulcerative Colitis

Eosinophils have been implicated in the pathogenesis of IBA (see Wedemeyer et al 2008 *Best Practice & Res Clin Gastroenterol* 22 (3):537-549, which is hereby incorporated by reference. Active inflammation has been associated with increased eosinophils at the site of inflammation. The release of their proteins (including eosinophil granule cationic protein) can cause tissue damage. Thus, lowering the level of eotaxin would result in a loss of eosinophil aggregation, leading to a reduction of symptoms of IBA, including inflammation.

Thus another aspect of this invention is a method to decrease the symptoms of irritable bowel syndrome by administering a eotaxin-reducing effective amount of 25-OH D3 to a person in need of such reduction. The resulting reduction of eosinophil aggregation would lead to an observable reduction in symptoms of IBA, including a decrease in inflammation. Another aspect of this invention is the use of 25-OH D3 in the method of making a medicament suitable for IBA.

The 25-OH D3 may be used as an adjunct to or in co-therapy with known IBA therapies.

Crohn's Disease and ulcerative colitis are chronic inflammatory diseases, but no specific pathogen has been identified Like IBS, they are characterized by increased levels of eosinophils. It has been shown that eotaxin-deficient mice had a reduced amount of eosinophils in the colon, and exhibit a significantly attenuated colitis compared to wild-type.

Thus another aspect of this invention is a method to decrease the symptoms of Crohn's Disease or ulcerative colitis by administering a eotaxin-reducing effective amount of 25-OH D3 to a person in need of such reduction. The resulting reduction of eosinophil aggregantion would lead to an observable reduction in symptoms of Crohn's disease or ulcerative colitis, including decrease in swelling and inflammation. Another aspect of this invention is the use of 25-OH D3 in the method of making a medicament suitable for Crohn's disease or ulcerative colitis.

The 25-OH D3 may be used as an adjunct to or in co-therapy with known Crohn's disease or ulcerative colitis therapies.

Other Gastrointestinal Conditions

Hogan et al 2004 *Aliment Pharmacol Ther* 20:1231-1240, which is hereby incorporated by reference, propose that reduction of eosinophils would be beneficial in other gastrointestinal conditions, including food allergies, parasitic infections, and gastro-esophageal reflux.

Dosages

Food Dosages:

The RDA which is in place at the time the food is sold is the maximum dosage of the combination of Vitamin D3+25-OH D3 recommended to be incorporated into a food Currently, the RDA for Vitamin D3 is:

400 IU for infants (0-12 months)

600 IU for children (+1 year) through adolescents and adults (70 years)

800 IU for adults (+71 years)

600 IU for pregnant or lactating women

The upper limit is 4000 IU.

For 25-OH D3 alone, there is not a current RDA, as in some countries, regulations do not permit it to be added to human food; however it is considered to be approximately 3× as active as Vitamin D3. Thus, for food use, the maximum dose which should be present in a food is approximately 3× less than the RDA of Vitamin D3. It is noted that conventionally Vitamin D3 dosages are expressed in IUs, whereas 25-OH D3 dosages are expressed in µg. The amounts are readily converted, as one IU Vitamin D3 is equal to 40 µg.

Pharmaceutical, Food Supplements, and Nutraceutical Dosages

Daily.

A composition according to this invention where the two active ingredients are to be administered separately, or alone contains Vitamin D or 25-OH D3 in an amount from about 1 µg to about 50 µg, preferably about 5 µg and 25 µg. Alternatively, a single daily dosage having both Vitamin D and 25-OH D3 contains each active ingredient in an amount from about 1 µg to about 50 µg, preferably about 5 µg and 25 µg.

The dosage ratio of Vitamin D to 25-OH D3 may be from about 50:1 to about 1:50, more preferably from about 25:1 to about 1:25, and even more preferably from about 6:1 to about 1:6.

Multiple, separate dosages may be packaged in a single kit (or container). For example, the kit may be comprised of thirty separate daily dosages of both actives separately (i.e. 60 separate dosages), or combined (i.e. 30 dosages containing both active ingredients). Instructions for administering the dosages to a human may be included in the kit.

Weekly.

A single weekly dosage contains Vitamin D or 25-OH D3 in an amount from about 7 µg to about 350 µg, and preferably from about 35 to 175 µg. Alternatively, a single weekly dosage may contain both Vitamin D and 25-OH D3 each in an amount from about 7 µg to about 350 µg, and preferably from about 35 to 175 µg. The dosage ratio of Vitamin D to 25-OH D3 may be from about 50:1 to about 1:50, more preferably from about 25:1 to about 1:25, and even more preferably from about 6:1 to about 1:6.

Monthly.

A single monthly dosage contains Vitamin D or 25-OH D3 in an amount from 30 µg to about 1500 µg, preferably about 75 µg to about 500 µg. Alternatively, a single monthly dosage may contain both Vitamin D and 25-OH D3 each in an amount from 30 µg to about 1500 µg, preferably about 75 µg to about 500 µg. A kit may be comprised of one, two, three, four, five, six, seven, eight, nine, ten, eleven, or twelve weekly or monthly dosages.

Dosage ratios of Vitamin D to 25-OH D3 should range between 50:1 to about 1:50, more preferably from about 25:1 to about 1:25, and even more preferably from about 6:1 to about 1:6.

Bolus:

A single bolus dosage contains Vitamin D or 25-OH D3 in an amount from 30 µg to about 7500 µg, Alternatively, a single bolus dosage may contain both Vitamin D and 25-OH D3 each in an amount from 100 µg to about 7500 µg, (preferably about 75 µg to about 3750 µg).

Dosage ratios of Vitamin D to 25-OH D3 should range between 50:1 to about 1:50, more preferably from about 25:1 to about 1:25, and even more preferably from about 6:1 to about 1:6.

Bolus dose can be followed by a daily or weekly or monthly regimen as described above.

There is a scarcity of data on the relationship between orally-administered 25-hydroxyvitamin D3 and its resulting systemic concentration in humans, in comparison to orally-administered vitamin D3. The most comprehensive analysis to date of the kinetics of vitamin D3 and 25-hydroxyvitamin D3 was conducted by Barger-Lux et al. (Osteoperosis 8:222-230, 1998). Healthy men were administered up to 1250 µg/day of vitamin D3 over a period of eight weeks, and up to 50 µg/day of 25-hydroxyvitamin D3 over a period of four weeks. Curvilinear kinetics were demonstrated for the relationship of vitamin D3 and plasma 25-hydroxyvitamin D3, and it was suggested that this may be due to saturation of hydroxylase activity in the liver. This was supported in that dosing with 25-hydroxyvitamin D3 was not reported as producing curvilinear kinetics (Barger-Lux et al., 1998). Although data on 25-hydroxyvitamin D3 does show curvilinear kinetics, it is only evident when the dose is extended past the level considered to result in maximum physiological benefit, which may indicate the activity of a homeostatic mechanism that is overwhelmed at very high doses. Within the physiological range, the relationship appears linear and comparable to Barger-Lux et al. These data indicate that a daily dose of between 10 µg and 60 µg of 25-hydroxyvitamin D is required for maximum health benefit.

A study of the pharmacokinetics in humans of orally-administered spray-dried 25-hydroxyvitamin D3, spray-dried vitamin D3, or both was initiated to investigate their physiological interactions. In particular, the shapes of their dose-response curves (which indicates the concentrations of vitamin D3 and 25-hydroxyvitamin D3 in the circulation over a set time course, not simply the average or maximum concentration achieved) and the steady-state kinetics were of interest. In respect of the former point, it is important to investigate the change in shape of the dose-response curves when exposure is to both vitamin D3 and 25-hydroxyvitamin D3. In respect of the latter point, it is also necessary to investigate their steady-state kinetics when dosing is less frequent than daily because this is the preferred regimen for groups that may have low compliance with taking daily supplements (such as the elderly).

The following non-limiting examples are presented to better illustrate the invention.

EXAMPLES

Example 1

Clinical Trial

Clinical Trial

Subjects

Healthy, postmenopausal women (50 to 70 years of age) were recruited using informed consent and screened using the following criteria: serum 25-hydroxy vitamin D3 between 20 nmol/L and 50 nmol/L, body mass index between 18 kg/m$^2$ and 27 kg/m$^2$, blood pressure less than 146/95 mm Hg, serum calcium less than 2.6 nmol/L, fasting glucose less than 100 mg/dl, no high-intensity exercise more than three times per week, no treatment for hypertension, no use of high-dose vitamin D or calcium supplement or drug affecting bone metabolism (e.g., biphosphonate, calcitonin, estrogen receptor modulator, hormone replacement therapy, parathyroid hormone), and not visiting a "sunny" location during the study.

Subjects were randomly assigned to one of seven treatment groups (i.e., daily, weekly, bolus as single dose, and bolus as combination dose). Each group included five subjects. They were followed for four months in Zurich, Switzerland during the winter.

Design

The objective was studying and comparing the pharmacokinetic characteristics of vitamin D3 and 25-hydroxyvitamin D3 administered to humans. Equimolar quantities of both substances were investigated. The regimen was based on 20 µg/day (or its equivalent on a weekly basis) of 25-hydroxyvitamin D3. For comparative purposes, it was necessary to administer equimolar quantities of either vitamin D3 or 25-hydroxyvitamin D3. In respect to administration of vitamin D3, the dose was considered to be sufficient to overcome background variability and provide and efficacious dose to the participants.

| | Daily: 120 administrations | |
|---|---|---|
| 1. | 25-Hydroxyvitamin D3 | 20 μg |
| 2. | Vitamin D3 | 20 μg (800 IU) |
| | Weekly: 16 administrations | |
| 3. | 25-Hydroxyvitamin D3 | 140 μg |
| 4. | Vitamin D3 | 140 μg (5600 IU) |
| | Bolus: single administration | |
| 5. | 25-Hydroxyvitamin D3 | 140 μg |
| 6. | Vitamin D3 | 140 μg (5600 IU) |
| | Bolus: combo administration | |
| 7. | D3 and 25(OH)D3 | 140 μg (5600 IU) + 140 μg |

Hard gel capsules, which are packaged in bottles, contain either 20 μg or 140 μg of either spray-dried vitamin D3 or 25-hydroxyvitamin D3 per capsule. Each dosage was consumed orally at breakfast. The duration of the study was four months for the "Daily" and "Weekly" groups. Subjects enrolled in the "Bolus" group consumed orally a single dosage at the second study visit.

Plasma concentrations of 25-hydroxyvitamin D3 (e.g., peak and steady state) were determined by obtaining samples from the subjects at various times after the dosage was ingested. For screening purposes and to establish baseline values, a blood sample was obtained prior to enrollment into the study and the clinical laboratory measured vitamin D3, 25-hydroxyvitamin D3, calcium, creatinine, albumin, and fasting glucose in the serum. On Monday of Week 1 of the study, pharmacokinetics of serum vitamin D3, 25-hydroxyvitamin D3, and 1,25-dihydroxy vitamin D3; serum markers (i.e., vitamin D3, 25-hydroxyvitamin D3, calcium, creatinine, albumin, PTH, GOT, GPT, ALP, triglycerides, HDL, LDL, total cholesterol, bALP, and fasting glucose); and urine markers (i.e., calcium, creatinine, and DPD) were assessed over 24 hours. Daily samples for the remaining days of Week 1 and Monday of Week 2 were taken to assess serum vitamin D3 and 25-hydroxyvitamin D3, serum markers (i.e., calcium, creatinine, albumin), and urine markers (i.e., calcium, creatinine). The assessments continued on Monday of Weeks 3, 5, 7, 9, 11, 13 and 15. On Monday of Week 16, samples were taken to assess pharmacokinetics of serum vitamin D3, 25-hydroxyvitamin D3, and 1,25-dihydroxy vitamin D3; serum markers (i.e., vitamin D3, 25-hydroxyvitamin D3, calcium, creatinine, albumin, PTH, GOT, GPT, ALP, triglycerides, HDL, LDL, total cholesterol, bALP, and fasting glucose); and urine markers (i.e., calcium, creatinine, and DPD).

Results

25-Hydroxyvitamin D3 Selectively Reduces Plasma Levels of Eotaxin

Twenty healthy postmenopausal women with 25-Hydroxyvitamin D3 levels below 25 ng/ml and a mean age of 61.5 years (SD ±7.2) were enrolled in this study. Participants were randomized to either 20 μg of oral 25-Hydroxyvitamin D3 or 20 μg of vitamin D3 per day in a double-blind manner. On 14 visits over 4 months, 25(OH)D levels, and 7 inflammation markers (eotaxin, IL-8, IL-12, IP-10, MCP-1, MP-1β, RANTES) were measured. All analyses were adjusted for baseline, age and body mass index.

Mean 25(OH)D levels increased from 13.7 to 69.5 ng/ml in the 25-Hydroxyvitamin D3 group (not shown). For vitamin D3, 25(OH)D levels increased from 13.5 to 31.0 ng/ml with a slow increase over time. Levels of inflammatory markers were determined at baseline and the end of the follow-up period. For most of the markers baseline levels vary considerably within a population of healthy individuals (see e.g. Campell et al Human Immunology vol 62, p. 668-678, 2001). Yet, they increase during periods of infection or health deteriorations. For instance eotaxin levels significantly increase in individuals during episodes of asthma or allergy (Campell et al. International Immunology vol. 14, p. 1255-1262, 2002). While both types of vitamin D supplementation contributed to a decrease in 5 out of 7 inflammation markers, only eotaxin levels were significantly more reduced by 25-Hydroxyvitamin D3 compared to vitamin D3 (p=0.003) at the end of the intervention phase. It should be noted that relative changes of different inflammatory markers ought be considered to reflect a positive impact on health rather than absolute levels, since these depend on the sensitivity of the analytical methods used.

The results demonstrate the selective effect of 25-Hydroxyvitamin D3 on the levels of the inflammatory marker eotaxin.

| | Vitamin $D_3$ | 25(OH)D | Difference |
|---|---|---|---|
| | Baseline | | |
| Plasma eotaxin level (pg/ml) | 27.86 (1.58) | 28.23 (1.63) | 0.36 (2.31) p = 0.88 |
| Plasma IL-8 level (pg/ml) | 2.62 (0.11) | 2.97 (0.14) | 0.35 (0.18) p = 0.05 |
| Plasma IL-12 level (pg/ml) | 4.25 (0.36) | 5.81 (0.29) | 1.56 (0.47) p = 0.001 |
| Plasma IP-10 level (pg/ml) | 292.54 (61.69) | 287.76 (60.33) | -4.78 (8.05) p = 0.96 |
| Plasma MCP-1 level (pg/ml) | 14.19 (1.21) | 14.24 (1.32) | 0.05 (1.82) p = 0.98 |
| Plasma MIP-1β level (pg/ml) | 29.17 (1.51) | 31.55 (1.69) | 2.38 (2.30) p = 0.30 |
| Plasma RANTES level (pg/ml) | 34.20 (8.81) | 41.63 (8.82) | 7.43 (2.86) p = 0.56 |
| | End of follow-up | | |
| Plasma eotaxin level (pg/ml) | 30.91 (1.61) | 21.07 (1.90) | -9.83 (2.56) p = 0.0002 |
| Plasma IL-8 level (pg/ml) | 1.55 (0.12) | 1.35 (0.11) | -0.20 (0.16) p = 0.22 |
| Plasma IL-12 level (pg/ml) | 2.63 (0.32) | 0.98 (0.18) | -1.64 (0.37) p < 0.0001 |
| Plasma IP-10 level (pg/ml) | 230.7 (59.8) | 279.3 (59.8) | 48.60 (86.45) p = 0.57 |
| Plasma MCP-1 level (pg/ml) | 12.11 (1.19) | 7.68 (1.21) | -4.42 (1.73) p = 0.01 |
| Plasma MIP-1β level (pg/ml) | 25.57 (1.79) | 19.85 (1.43) | -5.72 (2.31) p = 0.01 |
| Plasma RANTES level (pg/ml) | 26.68 (8.81) | 24.47 (8.82) | -2.21 (12.86) p = 0.86 |

We claim:

1. A method of decreasing eotaxin levels in a human at risk for or experiencing symptoms of a disease or condition characterized by increased levels of eotaxin consisting essentially of administering, to a human patient at risk of or experiencing increased levels of eotaxin from a disease or condition selected from the group consisting of allergic rhinitis, asthma, sinusitis and nasal polyps, an eotaxin-lowering effective amount consisting essentially of 25-OH D3, and observing a lessening of the eotaxin levels of the patient.

2. The method according to claim 1 wherein the administering is with a pharmaceutical formulation.

3. The method according to claim 1 wherein the administering is with a food or nutraceutical.

4. The method according to claim 1, which comprises administering the 25-OH D3 in an amount of 1 μg to 50 μg per day.

5. The method according to claim 1, which comprises administering the 25-OH D3 in an amount of 7 μg to 350 μg per week.

6. The method according to claim 1, which comprises administering the 25-OH D3 in an amount of 30 μg to 1,500 μg per month.

7. The method according to claim 1, which comprises administering the 25-OH D3 in a single bolus dosage of 30 μg to 7,500 μg.

8. A method of decreasing eotaxin levels in a human at risk for or experiencing symptoms of a disease or condition characterized by increased levels of eotaxin consisting essentially of administering, to a human patient at risk of or experiencing increased levels of eotaxin from a disease or condition selected from the group consisting of allergic rhinitis, asthma, sinusitis and nasal polyps, an eotaxin-lowering effective amount consisting of 25-OH D3, and observing a lessening of the eotaxin levels of the patient.

* * * * *